US009663562B2

(12) United States Patent
Kufe et al.

(10) Patent No.: US 9,663,562 B2
(45) Date of Patent: May 30, 2017

(54) COMPOSITIONS AND METHODS FOR TREATING CANCER

(71) Applicant: Dana-Farber Cancer Institute, Inc., Boston, MA (US)

(72) Inventors: Donald Kufe, Wellesley, MA (US); Surender Kharbanda, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/776,379

(22) PCT Filed: Mar. 13, 2014

(86) PCT No.: PCT/US2014/026408
§ 371 (c)(1),
(2) Date: Sep. 14, 2015

(87) PCT Pub. No.: WO2014/160368
PCT Pub. Date: Oct. 2, 2014

(65) Prior Publication Data
US 2016/0145313 A1    May 26, 2016

Related U.S. Application Data

(60) Provisional application No. 61/779,955, filed on Mar. 13, 2013.

(51) Int. Cl.
| | | |
|---|---|---|
| A61K 38/00 | (2006.01) |
| A61K 45/06 | (2006.01) |
| A61K 47/08 | (2006.01) |
| C07K 7/04 | (2006.01) |
| C07K 14/47 | (2006.01) |
| A61K 47/48 | (2006.01) |
| A61K 38/17 | (2006.01) |

(52) U.S. Cl.
CPC ...... *C07K 14/4727* (2013.01); *A61K 38/1735* (2013.01); *A61K 45/06* (2013.01); *A61K 47/48315* (2013.01); *A61K 38/00* (2013.01)

(58) Field of Classification Search
CPC .... A61K 38/00; A61K 38/1735; A61K 45/06; A61K 47/48315; A61K 47/08; C07K 14/4727; C07K 7/04; C07K 14/47
USPC ........................................ 514/19.3; 530/326
See application file for complete search history.

(56) References Cited

U.S. PATENT DOCUMENTS

2007/0154886 A1* 7/2007 Macina ................. C07K 14/47
435/6.14
2016/0168262 A1* 6/2016 Spriggs .............. C07K 16/3092
424/139.1

FOREIGN PATENT DOCUMENTS

WO    WO 2004/053079 A2    6/2004

OTHER PUBLICATIONS

Boohaker et al., "The Use of Therapeutic Peptides to Target and to Kill Cancer Cells," *Current Medicinal Chemistry* (2012) 19 (22): 3794-3804.
Bouanene et al., "Conflicting views on the molecular structure of the cancer antigen CA125/MUC16," *Disease Markers* (2010) 28 (6): 385-394.
Haridas et al., "MUC16: molecular analysis and its functional implications in benign and malignant conditions," *Faseb Journal* (2014) 28 (10): 4183-4199.
Josh et al., "MUC1 oncoprotein is a druggable target in human prostate cancer cells," *Molecular Cancer Therapeutic* (2009) 8 (11): 3056-3065.
Raina et al., "Targeting cysteine-mediated dimerization of the MUC1-C oncoprotein in human cancer cells," *International Journal of Oncology* (2012) 40 (5): 1643-1649.
Uchida et al., "Inhibition of the MUC1-C oncoprotein is synergistic with cytotoxic agents in the treatment of breast cancer cells," *Cancer Biology & Therapy* (2013) 14 (2): 127-134.
Yin et al., "Terminal differentiation of chronic myelogenous leukemia cells is induced by targeting of the MUC1-C oncoprotein," *Cancer Biology & Therapy* (2010) 10 (5): 483-491.

* cited by examiner

*Primary Examiner* — Julie Ha
(74) *Attorney, Agent, or Firm* — Cooley LLP; Ivor R. Elrifi; Cynthia A. Kozakiewicz

(57) ABSTRACT

Compositions comprising SEQ ID NO: 1 and methods of treating a MUC16-expressing tumor cell are described.

20 Claims, 1 Drawing Sheet

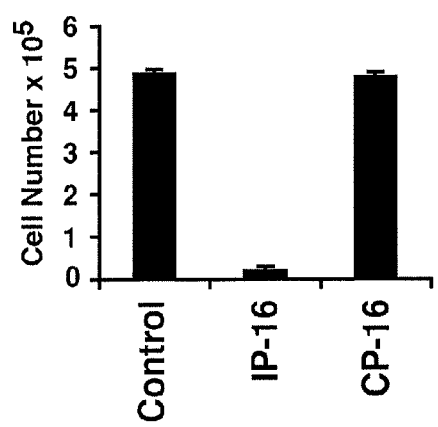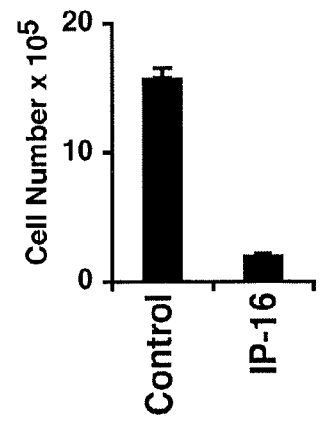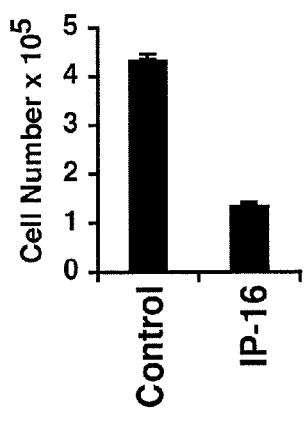

COMPOSITIONS AND METHODS FOR TREATING CANCER

RELATED APPLICATIONS

This application is a national stage application filed under 35 U.S.C. §371, of International Application No. PCT/US2014/026408, filed Mar. 13, 2014 which claims priority to, and benefit of, the U.S. Provisional Application No. 61/779,955, filed on Mar. 13, 2013, the contents of which are incorporated herein by reference in their entireties.

GOVERNMENT INTEREST

This invention was made with government support under grant number R01CA097098 awarded by The National Institutes of Health. The government has certain rights in the invention.

INCORPORATION OF SEQUENCE LISTING

The contents of the file named "DFCI-072 N01 US V1 322270-2508_ST25.txt", which was created on Oct. 27, 2015 and is 3 KB in size, are hereby incorporated by reference in their entirety.

FIELD OF THE INVENTION

The present invention relates generally to composition and methods of treating cancer. Also included are methods of identifying therapeutic targets for the treatment of cancer.

BACKGROUND OF THE INVENTION

Mucins are extensively O-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 16 can also signal to the interior of the cell through its cytoplasmic domain.

Available evidence indicates that human carcinomas have exploited MUC16 function in promoting tumorigencity. In this context, with transformation and loss of polarity, MUC16 is expressed at high levels on the entire cell surface in carcinomas of the ovaries. Other work has shown that overexpression of MUC16 confers anchorage-independent growth and tumorigenicity.

Thus a need exists for compounds that selectively target and kill MUC16 expressing tumors.

SUMMARY OF THE INVENTION

The invention provides MUC16 peptides. In some embodiments the MUC16 peptide contains the four consecutive MUC amino acids CLIC (SEQ ID NO: 3). For example, the peptide has the amino acid sequence XLIXGVLVTTRRRKK (SEQ ID NO:1) or CLICGVLVTTRRRKK (SEQ ID NO:2). The X is a cysteine, a penicillamine, homocysteine or 3-mercaptoproline.

In some aspects the peptide comprises all L amino acids, all D amino acids or a mixture of L and D amino acids. The peptide is covalently linked to a cell delivery domain or a cell transduction domain. The cell transduction domain is for example, an HIV tat cell transduction domain. The cell delivery domain is for example, a poly-D-R, poly D-P or poly D-K.

Also included in the invention are compositions containing the peptides according to the invention and a pharmaceutically acceptable carrier, buffer or diluent.

The invention further includes methods of inhibiting the growth of a MUC16 positive tumor cell in a subject, by administering to the subject a peptides according to the invention.

The tumor is an ovarian tumor, a pancreatic tumor, an esophageal tumor, a gastric tumor, or a colon tumor. The administering is local, regional, systemic or continual administration. In various aspects the method further includes administering to the subject a second anti-cancer therapy. The second anti-cancer therapy is for example, surgery, chemotherapy, radiotherapy, hormonal therapy, toxin therapy, immunotherapy, or cryotherapy. The second anti-cancer therapy is administered prior to, after or concurrently with the peptide.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1 illustrates the Effects of MUC16 Inhibitor Peptide (IP-16) on MUC16-positive cancer cells. Human MUC16-positive OVCAR3 ovarian cancer (A), MIAPACA2 pancreatic cancer (B) and ASPC1 pancreatic cancer (C) cells were left untreated (Control) or treated with 5 microM IP-16 (RRRRRRRR-CLICGVLVTTRRRKK; SEQ ID NO:5) or CP-16 (RRRRRRRR-ALIAGVLVTTRRRKK; SEQ ID NO:6) for 5 days. Viable cell number was determined by trypan blue staining. The results are expressed as cell number (mean+SD of three determinations). As a control, IP-16 had little, if any, effect on growth of human MUC16-negative HEK293T cells.

DETAILED DESCRIPTION OF THE INVENTION

The invention is based in part upon the discovery of a cell penetrating peptide derived from mucin 16 (MUC16) that selectively kills MUC16 expressing cells but not MUC16 null cells.

Mucin 16 is a membrane-associated mucin that possesses a single transmembrane domain. MUC16 is also known as CA-125 (cancer antigen 125 or carbohydrate antigen 125). CA-1265 is used as a biomarker in the detection of ovarian cancer.

A unique property of MUC16 is its large size. MUC16 is more than twice as long as MUC1 and MUC4 and contains about 22,000 amino acids, making it the largest membrane associated mucin. MUC16 is made of three different domains; an N-terminal domain, a tandem repeat domain, and a C-terminal domain. The N-terminal domain and tandem repeat domain are both entirely extracellular and highly O-glycosylated. All mucins contain a tandem repeat domain that has repeating sequences high in serine, threonine and proline. The C-terminal domain contains multiple extracellular SEA (sea urchin sperm protein, enterokinase, and agrin) modules, a transmembrane domain, and a cytoplasmic tail. The extracellular region of MUC16 can be released from the cell surface by undergoing proteolytic cleavage. MUC16 is thought to be cleaved at a site in the SEA modules.

MUC16 is a component of the ocular surface (including the cornea and conjunctiva) and the respiratory tract and female reproductive tract epithelia. Since MUC16 is highly glycosylated it creates a hydrophilic environment that acts as a lubricating barrier against foreign particles and infectious agents on the apical membrane of epithelial cells. The cytoplasmic tail of MUC16 has been shown to interact with cytoskeleton by binding members of the ERM protein family. The expression of mucin 16 has been shown to be altered in dry eye, cystic fibrosis, and several types of cancers. In particular MUC16 is aberrantly expressed in ovarian, pancreatic, esophageal, gastric and colon cancers. In cancer, MUC16 promotes growth, motility, invasiveness, tumorigenicity and metastases.

MUC16 Peptides

The present invention contemplates the design, production and use of various MUC16 peptides. The peptides have no more than 50, no more that 40, no more than 30, no more than 20 consecutive residues of MUC16. The peptides may have at least one non-MUC16 amino acid residue attached to the NH2-terminus or the COOH-terminus that may be useful in attaching the peptide to a solid surface, a tag sequence for purification, a stabilizing sequence, or a cell delivery domain.

In general, the peptides will be 150 residues or less, 100 residue or less or 50 residues or less again, comprising no more than 50 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 5-50 residues, 6-50 residues, 7-50 residues, 7-25, residues, 4-20 residues, 5-20 residues, 6-20 residues, 7-20 residues, and 7-15 residues are contemplated. The number of consecutive MUC16 residues may be 4, 5, 6, 7, 8, 9, 10, 11, 12, 13, 14, 15, 16, 17, 18, 19, 20, 25, 30, 35, 40, 45, or 50. Ranges of consecutive residues of 4-20 residues, 5-20 residues, 6-20 residues, 7-20 residues and 4-15 residues, 5-15, residues, 6-15 residues or 7-15 residues are contemplated.

In preferred embodiments the MUC16 peptide comprises the four consecutive MUC16 amino acids CLIC (SEQ ID NO:3).

An exemplary MUC16 peptide includes the amino acid sequence XLIXGVLVTTRRRKK (SEQ ID NO:1) or XLIXX$_1$ X$_1$ X$_1$ X$_1$ X$_1$ X$_1$RRRKK (SEQ ID NO:4) The X is a cysteine, a penicillamine, homocysteine or 3-mercaptoproline and the X$_1$ is any amino acid. A preferred MUC16 peptide includes the amino acid sequence CLICGVLVTTRRRKK (SEQ ID NO:2).

The present invention may utilize L-configuration amino acids, D-configuration amino acids, or a mixture thereof. The "L" and "D" convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

The present invention further contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine residues). Of particular interest are poly-D-Arg and poly-D-Lys sequences (e.g., dextrorotary residues, eight residues in length).

In other aspects of the invention the peptides are modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

In further aspects of the invention the peptides are modified for in vivo use by the addition of a moiety at amino- and/or carboxyl-terminal ends to facilitate the peptide attachment to a solid support such as a nanoparticle.

The peptides are produced for example by using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

In certain embodiments, one or more amino acids of the MUC16 peptides can be replaced by a non-naturally occurring amino acid or a naturally or non-naturally occurring amino acid analog. There are many amino acids beyond the standard 20 (Ala, Arg, Asn, Asp, Cys, Gln, Glu, Gly, His, Ile, Leu, Lys, Met, Phe, Pro, Ser, Thr, Trp, Tyr, and Val). Some are naturally-occurring others are not. (See, for example, Hunt, The Non-Protein Amino Acids: In Chemistry and Biochemistry of the Amino Acids, Barrett, Chapman and Hall, 1985). For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH3, —OH, —CH2NH3, —C(O)H, —CH2CH3, —CN, —CH2CH2CH3, —SH, or another group. Any amino acid can be substituted by the D-form of the amino acid.

With regard to non-naturally occurring amino acids or naturally and non-naturally occurring amino acid analogs, a number of substitutions in the polypeptide and agonists described herein are possible alone or in combination.

For example, glutamine residues can be substituted with gamma-Hydroxy-Glu or gamma-Carboxy-Glu. Tyrosine residues can be substituted with an alpha substituted amino acid such as L-alpha-methylphenylalanine or by analogues such as: 3-Amino-Tyr; Tyr(CH3); Tyr(PO3(CH3)2); Tyr (SO3H); beta-Cyclohexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp. Proline residues can be substituted with homopro (L-pipecolic acid); hydroxy-Pro; 3,4-Dehydro-Pro; 4-fluoro-Pro; or alpha-methyl-Pro or an N(alpha)-C (alpha) cyclized amino acid analogues with the structure: n=0, 1, 2, 3 Alanine residues can be substituted with alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of unnatural amino acids include: an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}C$, $^{15}N$, or $^{18}O$); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α disubstituted amino acid; a β-amino acid; a cyclic amino acid other than proline; an O-methyl-L-tyrosine; an L-3-(2-naphthyl)alanine; a 3-methyl-phenylalanine; a ρ-acetyl-L-phenylalanine; an O-4-allyl-L-tyrosine; a 4-propyl-L-tyrosine; a tri-O-acetyl-GlcNAc β-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl)alanine; D-3-(2-naphthyl)alanine (dNal); an amino-, isopropyl-, or O-allyl-containing phenylalanine analogue; a dopa, 0-methyl-L-tyrosine; a glycosylated amino acid; a p-(propargyloxy) phenylalanine; dimethyl-Lysine; hydroxy-proline; mercaptopropionic acid; methyl-lysine; 3-nitro-tyrosine; norleucine; pyro-glutamic acid; Z(Carbobenzoxyl); ε-Acetyl-Lysine; β-alanine; aminobenzoyl derivative; aminobutyric acid (Abu); citrulline; aminohexanoic acid; aminoisobutyric acid (AIB); cyclohexylalanine; d-cyclohexylalanine; hydroxyproline; nitro-arginine; nitro-phenylalanine; nitro-tyrosine; norvaline; octahydroindole carboxylate; ornithine (Orn); penicillamine (PEN); tetrahydroisoquinoline; acetamidomethyl protected amino acids and pegylated amino acids. Further examples of unnatural amino acids and amino acid analogs can be found in U.S. Application Nos. 2003/0108885, 2003/0082575, and 2006/0019347 (paragraphs 410-418) and the references cited therein. The polypeptides of the invention can include further modifications including those described in U.S. Application No. 2006/0019347, paragraph 589.

In some embodiments, an amino acid can be replaced by a naturally-occurring, non-essential amino acid, e.g., taurine.

In some MUC16 peptides one or both Cys residues can be replaced by homocysteine, penicillamine, 3-mercaptoproline (Kolodziej et al. 1996 Int J Pept Protein Res 48:274); β,βdimethylcysteine (Hunt et al. 1993 Int J Pept Protein Res 42:249) or diaminopropionic acid (Smith et al. 1978 J Med Chem 2 1:117) to form alternative internal cross-links at the positions of the normal disulfide bonds.

In addition, one or more disulfide bonds can be replaced by alternative covalent cross-links, e.g., an amide linkage (—CH2CH(O)NHCH2- or —CH2NHCH(O)CH2-), an ester linkage, a thioester linkage, a lactam bridge, a carbamoyl linkage, a urea linkage, a thiourea linkage, a phosphonate ester linkage, an alkyl linkage (—CH2CH2CH2CH2-), an alkenyl linkage (—CH2CH=CHCH2-), an ether linkage (—CH2CH2OCH2- or —CH2OCH2CH2-), a thioether linkage (—CH2CH2SCH2- or —CH2SCH2CH2-), an amine linkage (—CH2CH2NHCH2- or —CH2NHCH2CH2-) or a thioamide linkage (—CH2CH(S)HNHCH2- or —CH2NHCH(S)CH2-). For example, Ledu et al. (Proc Nat'l Acad. Sci. 100:11263-78, 2003) describe methods for preparing lactam and amide cross-links.

The MUC16 peptides can have one or more conventional polypeptide bonds replaced by an alternative bond. Such replacements can increase the stability of the polypeptide. For example, replacement of the polypeptide bond between a residue amino terminal to an aromatic residue (e.g. Tyr, Phe, Trp) with an alternative bond can reduce cleavage by carboxy peptidases and may increase half-life in the digestive tract. Bonds that can replace polypeptide bonds include: a retro-inverso bond (C(O)—NH instead of NH—C(O); a reduced amide bond (NH—CH2); a thiomethylene bond (S—CH2 or CH2-S); an oxomethylene bond (0-CH2 or CH2-O); an ethylene bond (CH2-CH2); a thioamide bond (C(S)—NH); a trans-olefine bond (CH=CH); a fluoro substituted trans-olefine bond (CF=CH); a ketomethylene bond (C(O)—CHR or CHR—C(O) wherein R is H or CH3; and a fluoro-ketomethylene bond (C(O)—CFR or CFR—C(O) wherein R is H or F or CH3.

Linkers or cross-linking agents may be used to fuse MUC16 peptides to other proteinaceous sequences, nanoparticles, or other solid supports. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., *Journal of the American Chemical Society*, 2000. 122(24): p. 5891-5892.

The present invention focuses on peptides comprising the sequence CLIC (SEQ ID NO:3). Having identified this key structure in MUC16, the inventors also contemplate that variants of the CLIC sequence (SEQ ID NO:3) may be employed. For example, certain non-natural amino acids that satisfy the structural constraints of the CLIC sequence (SEQ ID NO:3) may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography. X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790, 421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy. Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety.

Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Treatment Methods

Peptides or analogs that inhibit MUC16 oligomer formation are generally useful as anti-cancer therapeutics or prophylactics. They can be administered to mammalian subjects (e.g., human breast cancer patients) alone or in conjunction with other drugs and/or radiotherapy. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

Cancer cells to which the methods of the present invention can be applied include generally any cell that expresses MUC16, and more particularly, that overexpresses MUC16. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

When the methods are applied to subjects with cancer, prior to administration of a compound, the cancer can optionally be tested for MUC16 expression (MUC16 protein or MUC16 mRNA expression) by methods known in the art. In this way, subjects can be identified as having a MUC16-expressing or overexpressing cancer. Such methods can be performed in vitro on cancer cells obtained from a subject. Alternatively, in vivo imaging techniques using, for example, radiolabeled antibodies specific for MUC16 can be performed. In addition, body fluids (e.g., blood or urine) from subjects with cancer can be tested for elevated levels of MUC16 protein or MUC16 protein fragments.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

In some embodiments, the present invention provides use of a peptide (e.g., SEQ ID NOs: 1-6) or a composition described herein in the manufacture of a medicament for inhibiting the growth of a MUC16 positive tumor cell in a subject.

In some embodiments, the present invention provides use of any peptide (e.g., SEQ ID NOs: 1-6) or any composition described herein for inhibiting the growth of a MUC16 positive tumor cell in a subject.

In some embodiments, the present invention provides a peptide (e.g., SEQ ID NOs: 1-6) or a composition described herein for inhibiting the growth of a MUC16 positive tumor cell in a subject.

Combination Therapies

Tumor cell resistance to DNA damaging agents represents a major problem in clinical oncology. One goal of current cancer research is to find ways to improve the efficacy of chemo- and radiotherapy. One way is by combining such traditional therapies with gene therapy. In the context of the present invention, it is contemplated that MUC16 peptide therapy could be used similarly in conjunction with chemotherapeutic, radiotherapeutic, or immunotherapeutic intervention.

To kill cells, inhibit cell growth, inhibit metastasis, inhibit angiogenesis or otherwise reverse or reduce the malignant phenotype of tumor cells, using the methods and compositions of the present invention, one would generally contact a target cell with a MUC16 peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the MUC16 peptide and the other includes the agent.

Alternatively, the MUC16 treatment may precede or follow the other treatment by intervals ranging from minutes to weeks. In embodiments where the other treatment and the MUC16 peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

To achieve cell killing, both therapies are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are contemplated for use with in combination with peptides of the present invention. For example, selective estrogen receptor antagonists ("SERMs"), such as Tamoxifen, 4-hydroxy Tamoxifen (Afimoxifene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC16 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of MUC16 peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

In addition to combining MUC16 therapies with chemo- and radiotherapies, it also is contemplated that combination with immunotherapy, hormone therapy, toxin therapy and surgery. In particular, one may employ targeted therapies such as Avastin, Erbitux, Gleevec, Herceptin and Rituxan.

Antibodies

Also included in the invention are antibodies that specifically bind to the MUC16 peptides of the invention.

The term "antibody" is used in the broadest sense and specifically covers monoclonal antibodies (including full length monoclonal antibodies), polyclonal antibodies, multispecific antibodies (e.g., bispecific antibodies), and antibody fragments, so long as they exhibit the desired biological activity.

Methods for generating polyclonal antibodies are well known in the art. Briefly, a polyclonal antibody is prepared by immunizing an animal with an antigenic composition and collecting antisera from that immunized animal. A wide range of animal species can be used for the production of antisera including rabbit, mouse, rat, hamster, guinea pig and goat.

As is well known in the art, a given composition may vary in its immunogenicity. It is often necessary therefore to boost the host immune system, as may be achieved by coupling a polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine. As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The serum for an immunized animal may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed polypeptide. The immunizing composition is administered in a manner that effectively stimulates antibody producing cells.

The methods for generating monoclonal antibodies (MAbs) generally begin along the same lines as those for preparing polyclonal antibodies. The use of rats may provide certain advantages (Goding, 1986), but mice are preferred, with the BALB/c mouse being the most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred. Often, a panel of animals will have been immunized and the spleen of animal with the highest antibody titer will be removed and obtaining lymphocytes from the spleen.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas). Selected hybridomas are serially diluted and cloned into individual antibody-producing cell lines, which can then be propagated indefinitely to provide MAbs.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated synthesizer, or by expression of full-length gene or of gene fragments in *E. coli* or other recombinant microorganisms and cell lines.

The present invention also encompasses various antibody conjugates. Conjugates with fluorescein markers are prepared be methods known in the art, such as conjugation in the presence of coupling agents or by reaction with an isothiocyanate. Conjugates with metal chelates are similarly produced. Other moieties to which antibodies may be conjugated include radionuclides such as 131I, 90Y, 105Rh, 47Sc, 67Cu, 212Bi, 211At, 188Re, 109Pd, 47Sc, 212Pb, and 153Sm and the like, as described in Gansow, 1991, which is herein incorporated by reference.

Monoclonal antibodies of the invention can also be coupled to conventional chemotherapeutic agents such as an antimetabolite, an anthracycline, a vinca alkaloid, an antibiotic or an alkylating agent. Drugs that may be coupled to the antibodies for targeting include compounds such as doxorubicin, cyclophosphamide, cisplatin, adriamycin, estramustine, fluorouracil, ethinyl estradiol, mitoxantrone, methotrexate, finasteride, taxol, and megestrol. Methods of coupling may be direct via covalent bonds, or indirect via linking molecules, and will generally be known in the art for the particular drug selected and are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bisazido compounds such as his (R-azidobenzoyl) hexanediamine, bisdiazonium derivatives such as bis-(R-diazoniumbenzoyl)ethylenediamine, diisocyanates such as tolylene 2,6-diisocyanate, and bis-active fluorine compounds such as 1,5-difluoro-2,4-dinitrobenzene. (See, e.g., Thorpe et al., 1982, herein incorporated by reference).

The antibodies of the present invention may also be conjugated with various toxin molecules or an effector such as IgG1 immunoglobulin, which induces cytolytic or cytotoxic immune response. Thus, the two components may be chemically bonded together by any of a variety of well-known chemical procedures. For example, the linkage may be by way of heterobifunctional cross-linkers, e.g. SPDP, carbodiimide, glutaraldehyde, or the like. The toxin molecules may also be fused to the antibody or binding regions thereof by recombinant means, such as through the production of single chain antibodies. The genes encoding protein chains may be cloned in cDNA or in genomic form by any cloning procedure known to those skilled in the art (see e.g., Sambrook et al., 1989). The recombinant production of various immunotoxins is well-known within the art and can be found, for example in Thorpe et al., 1982(a), Waldmann, 1991, and Pastan et al., 1992, all herein incorporated by reference. A variety of toxin molecules are suitable for use as the cytotoxic domain in the antibody conjugates or fusion proteins described here. Any toxin known to be useful as the toxic component of an immunotoxin may be used, preferably a protein toxin that may be recombinantly expressed. Particularly useful as the cytotoxic domain are bacterial toxins such as Pseudomonas exotoxin A (PE), diphtheria toxin, shiga toxin and shiga-like toxin, and ribosome inactivating toxins derived from plants and fungi, including ricin, α-sarcin, restrictotocin, mitogellin, tricanthosin, saporin-G, saporin-1, momordin, gelonin, pokeweed antiviral protein, abrin, modeccin and others described in Genetically Engineered Toxins, ed. A. Frankel, Marcel Dekker, Inc., 1992, herein incorporated by reference, and any recombinant derivatives of those proteins (see Olsnes 1981; U.S. Pat. No. 4,675,382; and U.S. Pat. No. 4,894,443, herein incorporated by reference).

The antibody may also be a bispecific antibody which recognizes both the MUC16 and an antigen which promotes the release of a cytokine such as IL-1, TNF alpha and CD16, CD2, CD3 L.C. CD28, which in turn, will activate the release of IFN gamma or TNF alpha, respectively.

The MAb's of the present invention encompass chimeric Mabs, including, "humanized" forms of non-human (e.g., murine) Mabs. Humanized MAbs are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. (see Jones et al., 1986; Riechmann et al., 1988; and Presta, 1992). Fully human MAbs are preferred in the therapeutic methods of the present invention.

"Single-chain FV" or "sFv" antibody fragments of the present invention comprise the VH and VL domains of antibody, wherein these domains are present in a single polypeptide chain. Generally, the Fv polypeptide further comprises a polypeptide linker between the VH and VL domains which enables the sFv to form the desired structure for antigen binding (see Pluckthun, 1994).

Vaccines

The present invention also encompasses the use of MUC16 peptides, e.g., in a vaccine wherein the host mammal generates antibodies to the polypeptide which also act against the host's own MUC16. Vaccine preparation techniques are generally known in the art as described by Duffy (1980), and references cited therein, all of which are incorporated herein by reference.

The MUC16 peptides may be conjugated to a carrier molecule such as a protein or Ficoll. The carrier protein is preferably one with a molecular weight of at least about 40,000 dalton and more preferably at least about 60,000 dalton. The vaccine formulation may comprise a pharmaceutically acceptable carrier and may also include adjuvant systems for enhancing the immunogenicity of the formulation, such as oil-in water systems and other systems known in the art. Since the peptides or conjugates may be broken down in the stomach, the vaccine is preferably administered parenterally (for instance, subcutaneous, intramuscular, intravenous, or intradermal injection). The dosage will depend on the specific activity of the vaccine and can be readily determined by routine experimentation. The formulations may be presented in unit-dose or multi-dose containers, for example, sealed ampoules and vials and may be stored in a freeze-dried condition requiring only the addition of the sterile liquid carrier immediately prior to use.

EXAMPLE

The Effects of MUC16 Inhibitor Peptide (IP-16) on MUC16-Positive Cancer Cells

As shown in FIG. 1, human MUC16-positive OVCAR3 ovarian cancer (A), MIAPACA2 pancreatic cancer (B) and ASPC1 pancreatic cancer (C) cells were treated with control or 5 microM IP-16(RRRRRRRR-CLICGVLVTTRRRKK; SEQ ID NO:5) or CP-16 (RRRRRRRR-ALIAGVLVT-TRRRKK; SEQ ID NO:6) for 5 days. Viable cell number was determined by trypan blue staining. IP-16 significantly reduced the cell number of cancer cells. However, as a control, IP-16 had little, if any, effect on growth of human MUC16-negative HEK293T cells.

We claim:

1. A fusion peptide comprising:
   a cell delivery domain or a cell transduction domain, and
   a polypeptide comprising the amino acid sequence XLIXGVLVTTRRRKK (SEQ ID NO:1), wherein the polypeptide is less than 50 amino acids in length.

2. The fusion peptide of claim 1, wherein the polypeptide comprises the amino acid sequence CLICGVLVTTRRRKK (SEQ ID NO:2).

3. The fusion peptide of claim 1, wherein the polypeptide comprises all L-amino acids.

4. The fusion peptide of claim 1, wherein the polypeptide comprises all D-amino acids.

5. The fusion peptide of claim 1, wherein the polypeptide comprises a mixture of L- and D-amino acids.

6. The fusion peptide of claim 1, wherein the cell transduction domain is an HIV tat cell transduction domain.

7. The fusion peptide of claim 1, wherein the cell delivery domain is a poly-D-R, poly D-P, or poly D-K.

8. A composition comprising the fusion peptide of claim 1 and a pharmaceutically acceptable carrier, buffer, or diluent.

9. A method of inhibiting the growth of a MUC16 positive tumor cell in a subject, comprising administering to the subject a composition comprising:
   (a) a fusion peptide comprising:
      (i) a cell delivery domain or a cell transduction domain, and
      (ii) a polypeptide comprising the amino acid sequence XLIXGVLVTTRRRKK (SEQ ID NO: 1), wherein the polypeptide is less than 50 amino acids in length; and
   (b) a pharmaceutically acceptable carrier, buffer, or diluent.

10. The method of claim 9, wherein the tumor is an ovarian tumor, a pancreatic tumor, an esophageal tumor, a gastric tumor, or a colon tumor.

11. The method of claim 9, wherein the administering is local, regional, systemic, or continual administration.

12. The method of claim 9, further comprising administering to the subject a second anti-cancer therapy.

13. The method of claim 12, wherein the second anti-cancer therapy is surgery, chemotherapy, radiotherapy, hormonal therapy, toxin therapy, immunotherapy, or cryotherapy.

14. The method of claim 12, wherein the second anti-cancer therapy is administered prior to, after, or concurrently with the fusion peptide.

15. The method of claim 9, wherein the polypeptide comprises the amino acid sequence CLICGVLVTTRRRKK (SEQ ID NO:2).

16. The method of claim 9, wherein the polypeptide comprises all L-amino acids.

17. The method of claim 9, wherein the polypeptide comprises all D-amino acids.

18. The method of claim 9, wherein the polypeptide comprises a mixture of L- and D-amino acids.

19. The method of claim 9, wherein the cell transduction domain is an HIV tat cell transduction domain.

20. The method of claim 9, wherein the cell delivery domain is poly-D-R, poly D-P, or poly D-K.

* * * * *

SEQUENCE LISTING

<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: MISC_FEATURE

```
<222> LOCATION: (1)..(1)
<223> OTHER INFORMATION: X is a cysteine, a penicillamine, homcystein or
      3-mercaptoproline.
<220> FEATURE:
<221> NAME/KEY: MISC_FEATURE
<222> LOCATION: (4)..(4)
<223> OTHER INFORMATION: X is a cysteine, a penicillamine, homcystein or
      3-mercaptoproline.

<400> SEQUENCE: 1

Xaa Leu Ile Xaa Gly Val Leu Val Thr Thr Arg Arg Arg Lys Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Oligopeptide

<400> SEQUENCE: 2

Cys Leu Ile Cys Gly Val Leu Val Thr Thr Arg Arg Arg Lys Lys
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Synthetic Oligonucleotide

<400> SEQUENCE: 3

Cys Leu Ile Cys
1

<210> SEQ ID NO 4
<211> LENGTH: 15
<212> TYPE: PRT
<213> ORGANISM: Artificial Sequence
<220> FEATURE:
<223> OTHER INFORMATION: Synthetic Oligopeptide
<220> FEATURE:
<221> NAME/KEY: MISC_FEATURE
<222> LOCATION: (1)..(1)
<223> OTHER INFORMATION: X is a cysteine, a penicillamine, homcystein or
      3-mercaptoproline
<220> FEATURE:
<221> NAME/KEY: MISC_FEATURE
<222> LOCATION: (4)..(4)
<223> OTHER INFORMATION: X is a cysteine, a penicillamine, homcystein or
      3-mercaptoproline
<220> FEATURE:
<221> NAME/KEY: MISC_FEATURE
<222> LOCATION: (5)..(10)
<223> OTHER INFORMATION: X is any amino acid

<400> SEQUENCE: 4

Xaa Leu Ile Xaa Xaa Xaa Xaa Xaa Xaa Xaa Arg Arg Arg Lys Lys
1               5                   10                  15

<210> SEQ ID NO 5
<211> LENGTH: 23
<212> TYPE: PRT
<213> ORGANISM: Artificial Sequence
<220> FEATURE:
<223> OTHER INFORMATION: Synthetic Oligopeptide

<400> SEQUENCE: 5

Arg Arg Arg Arg Arg Arg Arg Arg Cys Leu Ile Cys Gly Val Leu Val
1               5                   10                  15
```

```
Thr Thr Arg Arg Arg Lys Lys
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic Oligopeptide

<400> SEQUENCE: 6

Arg Arg Arg Arg Arg Arg Arg Arg Ala Leu Ile Ala Gly Val Leu Val
1               5                   10                  15

Thr Thr Arg Arg Arg Lys Lys
            20
```